US009959857B2

(12) United States Patent
Chattell

(10) Patent No.: US 9,959,857 B2

(45) Date of Patent: May 1, 2018

(54) FLEXIBLE ACOUSTIC BARRIER

(71) Applicant: RVT Group Limited, Dartford (GB)

(72) Inventor: Timothy Chattell, Dartford (GB)

(73) Assignee: RVT GROUP LIMITED, Dartford (GB)

( * ) Notice: Subject to any disclaimer, the term of this patent is extended or adjusted under 35 U.S.C. 154(b) by 0 days. days.

(21) Appl. No.: 15/054,430

(22) Filed: Feb. 26, 2016

(65) Prior Publication Data

US 2016/0253987 A1 Sep. 1, 2016

(30) Foreign Application Priority Data

Feb. 27, 2015 (GB) .................................. 1503304.6

(51) Int. Cl.

| | |
|---|---|
| ***H04R 3/02*** | (2006.01) |
| ***H03B 29/00*** | (2006.01) |
| ***A61F 11/06*** | (2006.01) |
| ***G10K 11/16*** | (2006.01) |
| ***G10K 11/175*** | (2006.01) |
| ***G10K 11/162*** | (2006.01) |
| ***H04S 7/00*** | (2006.01) |
| *H04R 1/02* | (2006.01) |

(52) U.S. Cl.

CPC .......... *G10K 11/175* (2013.01); *G10K 11/162* (2013.01); *H04S 7/00* (2013.01); *H04R 1/02* (2013.01); *H04R 2201/021* (2013.01); *H04S 2420/01* (2013.01)

(58) Field of Classification Search

CPC ... G10K 11/175; H04R 1/02; H04R 2201/021

USPC ........... 381/73.1, 71.7, 71.6, 152, 71.1, 94.1

See application file for complete search history.

(56) References Cited

U.S. PATENT DOCUMENTS

| | | | | |
|---|---|---|---|---|
| 8,978,816 B2 * | 3/2015 | Slotznick | ................ | E04H 15/18 181/30 |
| 8,987,367 B2 * | 3/2015 | Sereboff | .................... | F24J 3/00 521/59 |
| 2001/0031052 A1 * | 10/2001 | Lock | ...................... | H04R 5/023 381/71.7 |

FOREIGN PATENT DOCUMENTS

| | | |
|---|---|---|
| EP | 1230637 B1 | 4/2010 |
| JP | 2008241899 A | 10/2008 |

OTHER PUBLICATIONS

GB Search report for GB1503304.6 dated Aug. 25, 2015.

* cited by examiner

*Primary Examiner* — Thjuan K Addy

(74) *Attorney, Agent, or Firm* — Finnegan, Henderson, Farabow, Garrett & Dunner, LLP

(57) ABSTRACT

A flexible acoustic barrier for suspending from a support frame wherein the flexible acoustic barrier comprises a portion of acoustic insulation material and at least one loudspeaker that is configured to emit an audible sound-masking signal to mask sound from a sound source. Another aspect of the invention comprises a corresponding method of mitigating noise pollution.

20 Claims, 3 Drawing Sheets

FLEXIBLE ACOUSTIC BARRIER

CROSS-REFERENCES TO RELATED APPLICATION

This application claims foreign priority benefits under 35 U.S.C. § 119 to GB application number 1503304.6 filed Feb. 27, 2015, which is incorporated by reference in its entirety.

TECHNICAL FIELD

The invention relates to a flexible acoustic barrier having a loudspeaker configured to emit an audible sound-masking signal.

BACKGROUND

Noise pollution, such as from construction machinery, can disturb or harm those near to the source of noise. It is known to mitigate the impact of noise sources, such as construction machinery, using acoustic barriers. Acoustic barriers may be assembled around and/or above a noise source to reduce the sound level of noise for persons in the surrounding environment.

Typically, the type of acoustic barrier that is provided to reduce the sound level of noise depends on the level of noise generated, and the maximum acceptable noise level for the particular environment. An acoustic barrier or acoustic barrier installation having the relevant performance characteristics is selected accordingly. The dominant performance characteristic is the level of noise reduction, and acoustic barriers of varying expense can be selected to achieve the desired performance characteristic by varying the thickness and composition of the barrier, amongst other things.

However, known acoustic barriers and acoustic barrier installations are configured to reduce the impact of the absolute noise level only, and fail to mitigate the disturbing influence of the residual noise.

Accordingly, it is desirable to provide an improved acoustic barrier.

SUMMARY

According to a first aspect of the invention there is provided a flexible acoustic barrier for suspending from a support frame, comprising: a portion of acoustic insulation material; and at least one loudspeaker configured to emit an audible sound-masking signal to mask sound from a sound source.

The sound source may be, for example, a construction site, transport infrastructure such as a road, equipment, people or any other source of sound.

The or each loudspeaker may be integrated in the portion of acoustic insulation material. For example, the loudspeaker may be provided in a cut-out within the portion of acoustic insulation material.

The acoustic barrier may further comprising an input port to receive a sound-masking signal for the at least one loudspeaker from a signal generator. The acoustic barrier may further comprise an output port for transmitting a sound-masking signal to a like acoustic barrier in a daisy-chain layout.

A cable coupling the input port with the loudspeaker and/or a cable coupling the output port with the loudspeaker may extend through a portion of the acoustic barrier. For example, the cable may extend through the portion of acoustic insulation material. A portion of the cable coupling the input port with the loudspeaker and/or a cable coupling the output port with the loudspeaker may extend from a body of the acoustic barrier so that the respective part can be manipulated relative the body, for example, so as to easily connect with a corresponding port of an adjacent barrier or a signal generator.

The cable may at least partly extend between the portion of acoustic insulation material and a body of the barrier to which the portion of acoustic insulation material is coupled. The portion of acoustic insulation material may be secured to the body so that the cable is securely retained between the portion of acoustic insulation material and the body.

The portion of acoustic insulation material may be secured to a substrate, such as a web or mesh, and a power or signal cable for the loudspeaker may be retained between the portion of insulating material and the substrate. Accordingly, the cable may be prevented from moving relative to the portion of insulating material and may be securely retained to prevent snagging.

The acoustic barrier may comprise a signal generator for generating a sound-masking signal for emission by the at least one loudspeaker. The sound-masking signal may comprise noise. The sound-masking signal may be selected from a group of noise signals consisting of: white noise, pink noise, brown noise, blue noise, violet noise and grey noise.

The acoustic barrier may be configured to be folded and/or to be rolled from a deployed configuration to a compact configuration.

There may be a plurality of portions of acoustic insulation material. The or each loudspeaker may be integrated in one of the portions of acoustic insulation, such as a lower portion, or different loudspeakers may be integrated in different portions of insulation material.

The or each portion of acoustic insulation material may be configured to reduce the sound level of a 70 decibel sound from the sound source by at least 10 decibels.

The or each portion of acoustic insulation material may have an acoustic absorption coefficient of at least 0.2, at least 0.3, at least 0.4 or at least 0.5 for frequencies in the range of 2 MHz to 10 MHz. The or each portion of acoustic insulation material may have an acoustic absorption coefficient of at least 0.1, at least 0.2 or at least 0.3 for frequencies in the range of 1 MHz to 10 MHz. The or each portion of acoustic insulation material may have an acoustic absorption coefficient of at least 0.02, 0.03, 0.04, or at least 0.05 for frequencies in the range of 0.2 MHz to 1 MHz.

The or each portion of acoustic insulation material may comprise a foam material, such as polyurethane (PU) foam. The foam may be a uniform open or closed cell foam. The foam may be have a waterproof or water repellent coating, or may otherwise be treated so as to be waterproof or water repellent. The or each portion of acoustic insulation material may be at least 25 mm thick.

The acoustic barrier may further comprise a body for mounting to a support frame, and the or each portion of acoustic insulation material may be mounted to or retained by the body.

The body may be flexible. The body may be a sheet, such as a substrate or backing, to which the or each portion of acoustic insulation material is mounted. The body may comprise front and/or back covers for the or each portion of acoustic insulation material. The body may comprise one or more pockets for receiving the or each portion of insulation material. The body may be composed of plastics material, such as polyvinylchloride (PVC). The body may be waterproof.

According to a second aspect of the invention there is provided an acoustic barrier installation comprising: at least one acoustic barrier in accordance with the first embodiment of the invention; and a support frame from which the or each acoustic barrier is suspended.

The acoustic barrier installation may further comprise a signal generator for generating the sound-masking signal for the or each loudspeaker of the or each acoustic barrier. The signal generator may be integrated into one of the acoustic barriers, or it may be structurally separate from the or each acoustic barriers and coupled to at least one acoustic barrier to provide the sound-masking signal to the or each acoustic barrier.

The acoustic barrier installation may further comprise a microphone for monitoring the sound environment of the acoustic barrier installation, and the signal generator or a controller for the signal generator may be configured so that the sound-masking signal for the or each loudspeaker is dependent on at least one characteristic of the sound environment based on an output signal from the microphone.

The signal generator or a controller for the signal generator may be configured so that the sound-masking signal for the or each loudspeaker is dependent on the power spectrum distribution (power spectral density) or the power intensity of the sound environment monitored by the microphone.

There may be at least two acoustic barriers and at least one of the acoustic barriers may comprise an output port for transmitting a sound-masking signal to a like acoustic barrier in a daisy-chain layout.

According to a third aspect of the invention there is also provided a kit of parts for an acoustic barrier installation in accordance with the second aspect of the invention, the kit of parts comprising at least one acoustic barrier in accordance with the first aspect of the invention and a signal generator.

According to a fourth aspect of the invention there is provided a method of mitigating noise pollution from a noise source, the method comprising: installing an acoustic barrier installation in accordance with the second aspect of the invention; generating a sound-masking signal for the or each loudspeaker of the installation; and audibly emitting the sound-masking signal using the or each loudspeaker to mask noise from the noise source.

The method may further comprise monitoring the sound environment using a microphone of the acoustic barrier installation and generating a sound-masking signal for the or each loudspeaker which is dependent on at least one characteristic of the sound environment, based on an output signal of the microphone. The sound-masking signal for the or each loudspeaker may be dependent on the power spectrum distribution or the power intensity of the sound environment monitored by the microphone.

According to a fifth aspect of the invention there is provided an acoustic barrier installation comprising: at least one acoustic barrier comprising a portion of acoustic insulation material; a support frame for the or each acoustic barrier; and at least one loudspeaker disposed above and spaced apart from the or each portion of acoustic insulation material.

The or each loudspeaker may be supported so that it is spaced apart from the or each portion of acoustic insulation material by at least 0.5 m, at least 0.75 m, at least 1 m, or at least 2 m. The or each loudspeaker may be supported on a speaker support, such as a post. The speaker support may be integrated with the support structure for the or each acoustic barrier. Alternatively, the speaker support may be integrated in the or each acoustic barrier, such as in the body of the acoustic barrier. The acoustic barrier may be flexible and may have any of the features described above.

BRIEF DESCRIPTION OF DRAWINGS

The invention will now be described, by way of example, with reference to the following drawings, in which.

DETAILED DESCRIPTION

Figure 1:
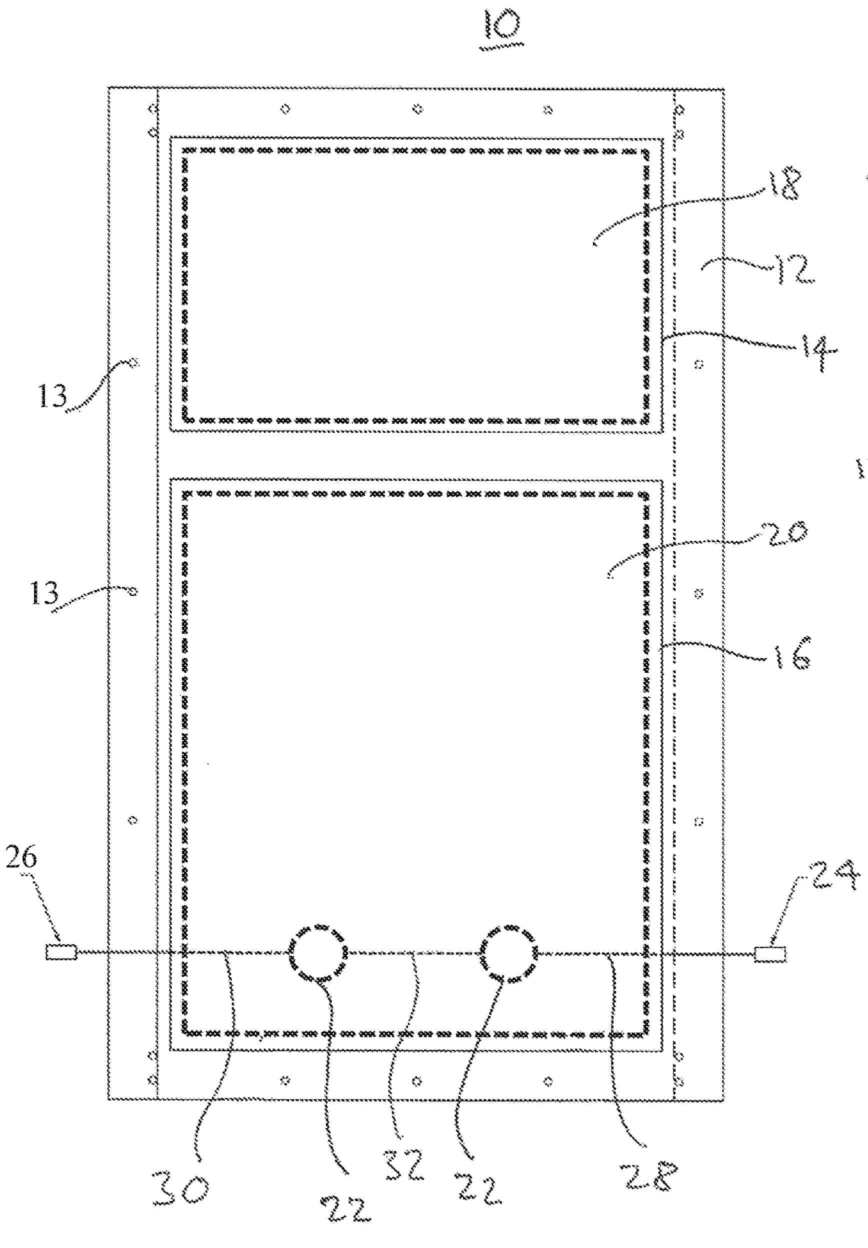
FIG. 1 schematically shows a front view of an acoustic barrier according to an embodiment of the invention.
Figure 2:
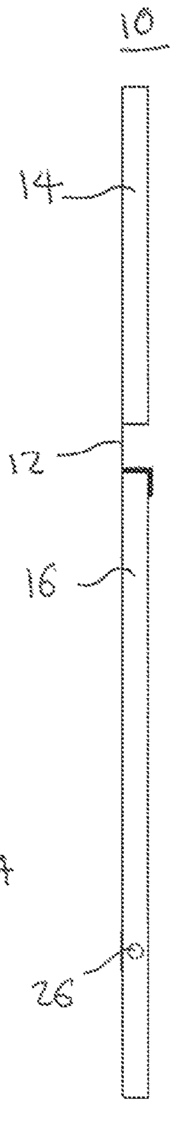
FIG. 2 schematically shows a side view of the acoustic barrier of FIG. 1.

FIGS. 1 and 2 show an acoustic barrier 10 in the form of a flexible acoustic curtain for suspending from a frame, such as a temporary scaffold.

The flexible acoustic curtain comprises a body 12 having a rectangular flexible polyvinylchloride (PVC) sheet and upper and lower pockets 14, 16 for retaining upper and lower portions 18, 20 of acoustic insulation material respectively. In this embodiment the pockets 14, 16 are also composed of flexible PVC material and can be stitched, welded, or otherwise fastened to the flexible PVC sheet of the body 12 to form part of the body 12.

The periphery of the body 12 is provided with eyelets 13 for securing the acoustic barrier to a support frame, for example, by a chord or security straps. In other embodiments, at least the lateral borders of the body 12 may be provided with hook and loop fasteners, or other fasteners, for quickly connecting adjacent acoustic barriers together.

Figure 3:
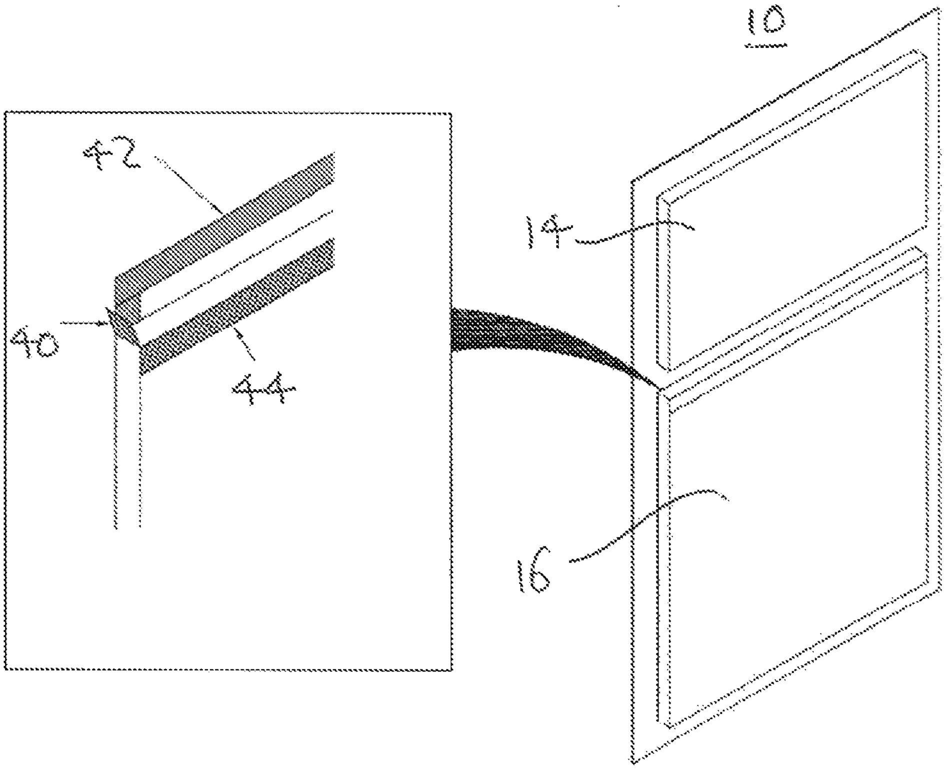
FIG. 3 schematically shows a perspective view of the acoustic barrier of FIG. 1, including a detail view of the pocket.

Each pocket 14, 16 is provided with a flap 40 for opening and closing the pocket, as shown in FIG. 3. In this embodiment, the flaps 40, 42 can be secured in a closed position using corresponding hook and loop fasteners provided on at least the upper flap 42 and the front portion 44 of each pocket 14, 16.

Referring again to FIG. 1, the portions of acoustic insulation material 18, 20 are received in the pockets 14, 16. In this embodiment, the portions of acoustic insulation material are composed of an open cell foam, for example a polyurethane foam having a density between 75 and 95 kg/m$^3$. In other embodiments, the foam may have a closed cell structure.

In this embodiment, the portions of acoustic insulation material 18, 20 are approximately 50 mm thick. The upper portion 18 has a width of approximately 1100 mm and a height of approximately 500 mm. The lower portion 20 has a width of approximately 1100 mm and a height of approximately 1200 mm.

The curtain can be folded, for example, at the gap between the two pockets 14, 16, so as to occupy less space. This can be useful for shipping or storing the product. Alternatively, the curtain can be rolled, as the portions of acoustic insulation material 18, 20 are flexible.

A sound-masking system is integrated with the curtain, and includes two loudspeakers 22, input and output ports 24, 26 provided with corresponding input and output cables 28, 30, and a connecting cable 32 extending between the two loudspeakers.

In this embodiment, each one of the loudspeakers 22 is integrated within the lower portion of acoustic insulation material 20. In particular, the lower portion 20 is provided with corresponding cutouts in which the loudspeakers 22 are received.

Figure 4:
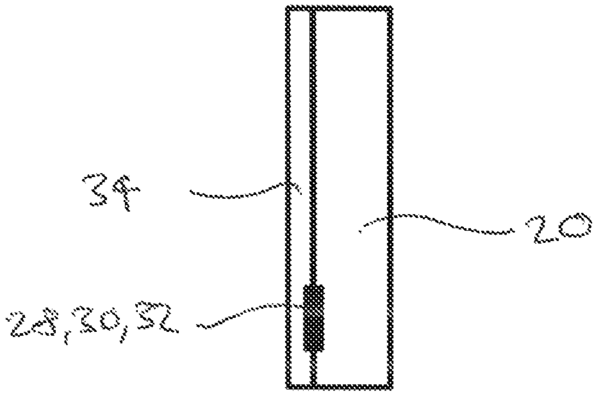
FIG. 4 schematically shows a cross-sectional view of a portion of a cabling arrangement between a portion of acoustic insulation material and a substrate.

The input and output cables 28, 30, and the connecting cable 32 extend laterally from the loudspeakers 22 along the rear face of the lower portion of acoustic insulation material 20, sandwiched between the lower portion 20 and a backing mesh 34, as shown in FIG. 4. In this example, the backing mesh is a flexible PVC mesh (or web) adhered to the lower portion of acoustic insulation material 20, so as to retain the cables 28, 30, 32 therebetween. In other embodiments, the backing mesh 34 may be replaced with an alternative layer, such as a layer of fabric, a layer of sheet PVC, or a second layer of acoustic insulation material.

In use, a plurality of acoustic barriers 10 are suspended from a support frame using the eyelets 13, such as a scaffold around a construction site, to reduce the sound level of noise from a noise source. The plurality of acoustic barriers 10 may be coupled together using the eyelets 13, or with hook and loop fasteners as described above.

A signal generator (not shown) is coupled to a first one of the acoustic barriers to provide a sound-masking signal for emission from the loudspeakers 22. The output port 26 of the first acoustic barrier 10 is coupled to the input port 24 of a like adjacent second acoustic barrier 10 in a daisy-chain layout so that the sound-masking signal is carried to each of the acoustic barriers 10 for emission by the respective loudspeakers 22.

The signal generator is configured to generate a sound-masking signal which has the effect of masking noise generated by a noise source (or other sounds which may not be considered to be noise) for those operating in the environment, by providing a background noise level. In this example embodiment, the signal generator is configured to generate a white noise sound-masking signal, which is a random signal characterised by having a constant power spectral density (i.e. the sound level is constant at all frequencies of the signal). White noise is considered to be particularly effective in masking noise generated by a noise source. In other example embodiments, the signal generator may be configured to generate other standard noise signals, such as pink noise and brown noise, in which the power spectral density is defined by standard specific rules (for example, for pink noise, the power spectral density is inversely proportional to frequency). In yet further embodiments, the signal generator may be configured to generate a customised sound-masking signal having a pre-determined power spectral density (or power distribution).

In yet further alternative embodiments, the signal generator may be configured to generate sound-masking signal dependent on the sound environment, for example, based on a signal from a microphone coupled to the signal generator. The sound-masking signal may be responsive to the sound environment, so as to mask the effect of particular noises from the sound environment that are detected by the microphone. For example the signal generate may generate a noise signal having a frequency range including the frequency of a noise within the sound environment, such as a particular piece of construction machinery.

Figure 5:
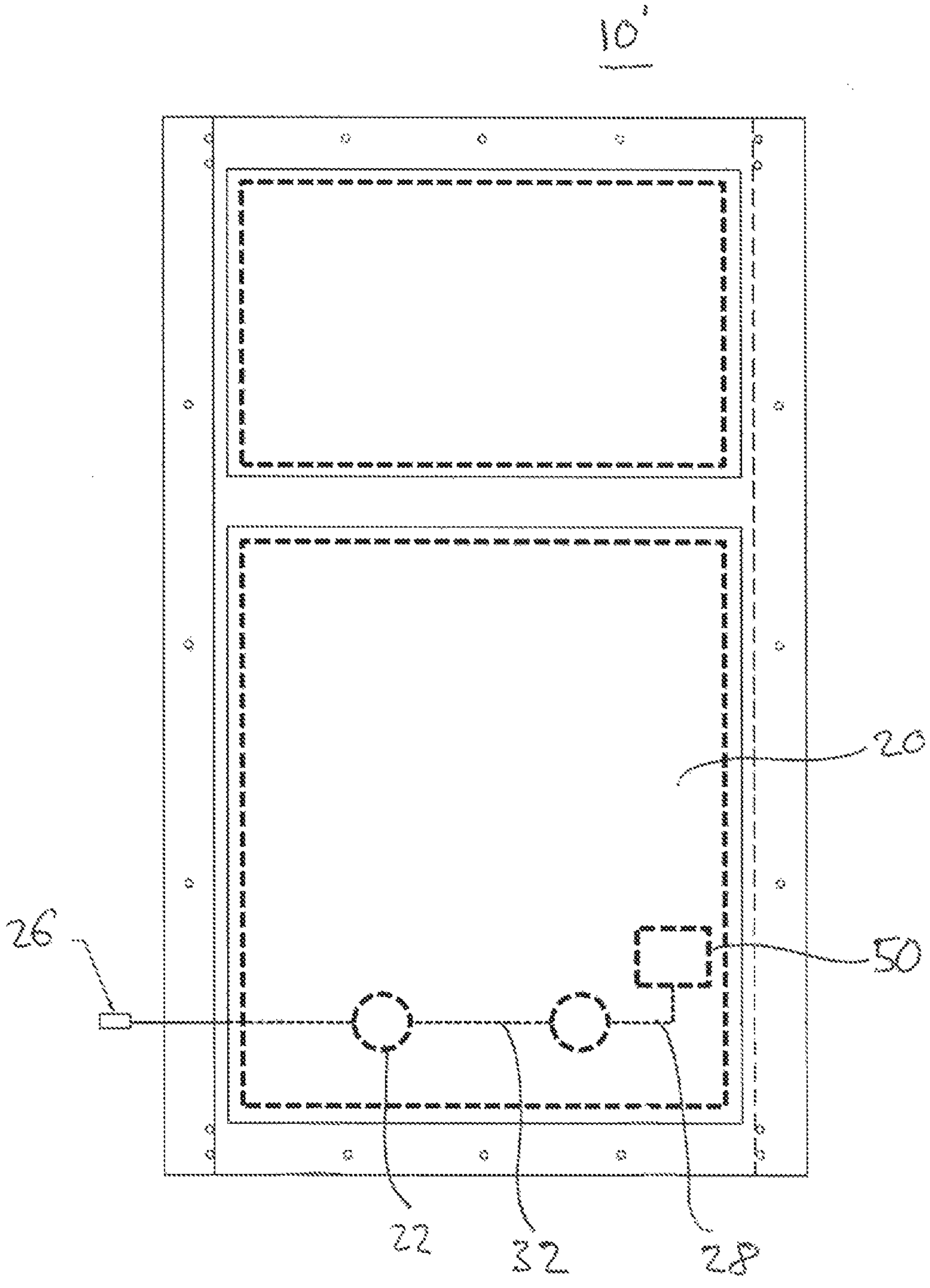
FIG. 5 shows a further embodiment of an acoustic barrier.

FIG. 5 shows a second embodiment of an acoustic barrier 10' which differs from the first embodiment described above only in that a signal generator 50 for the sound-masking signal is integrated in the acoustic barrier 10', in particular, within the lower portion of acoustic insulation material 20. The input cable extends directly between the signal generator 50 and the first of the two loudspeakers 22.

The invention claimed is:

1. A flexible acoustic barrier for suspending from a support frame, comprising:
   a portion of acoustic insulation material; and
   at least one loudspeaker configured to emit an audible sound-masking signal to mask sound from a sound source;
   wherein the acoustic barrier is configured to be folded, rolled, or folded and rolled from a deployed configuration to a compact configuration.

2. An acoustic barrier according to claim 1, wherein each loudspeaker is integrated in the portion of acoustic insulation material.

3. An acoustic barrier according to claim 1, further comprising an input port to receive a sound-masking signal for the at least one loudspeaker from a signal generator.

4. An acoustic barrier according to claim 1, wherein the acoustic barrier comprises an output port for transmitting a sound-masking signal to a like acoustic barrier in a daisy-chain layout.

5. An acoustic barrier according to claim 1, wherein the portion of acoustic insulation material is secured to a substrate, such as a web or mesh, and wherein a power or signal cable for the loudspeaker is retained between the portion of acoustic insulating material and the substrate.

6. An acoustic barrier according to claim 1, wherein the acoustic barrier comprises a signal generator for generating a sound-masking signal for emission by the at least one loudspeaker.

7. An acoustic barrier according to claim 6, wherein the sound-masking signal comprises noise.

8. An acoustic barrier according to claim 7, wherein the sound-masking signal is selected from a group of noise signals consisting of: white noise, pink noise, brown noise, blue noise, violet noise and grey noise.

9. An acoustic barrier according to claim 1, wherein there are a plurality of portions of acoustic insulation material.

10. An acoustic barrier according to claim 1, wherein the portion of acoustic insulation material is configured to reduce a sound level of a 70 decibel sound from the sound source by at least 10 decibels.

11. An acoustic barrier according to claim 1, wherein the portion of acoustic insulation material has an acoustic absorption coefficient of at least 0.5 for frequencies in a range of 2 MHz to 10 MHz.

12. An acoustic barrier according to claim 1, wherein the portion of acoustic insulation material comprises a foam material.

13. An acoustic barrier according to claim 1, further comprising a body for mounting to a support frame, and wherein the portion of acoustic insulation material is mounted to or retained by the body.

14. An acoustic barrier installation comprising:
   at least one acoustic barrier in accordance with claim 1; and
   a support frame from which each acoustic barrier is suspended.

15. An acoustic barrier installation according to claim 14, further comprising a signal generator for generating the sound-masking signal for each loudspeaker of each acoustic barrier.

16. An acoustic barrier installation according to claim 15, further comprising a microphone for monitoring a sound environment of the acoustic barrier installation, and wherein the signal generator or a controller for the signal generator is configured so that the sound-masking signal for each loudspeaker is dependent on at least one characteristic of the sound environment based on an output signal from the microphone.

17. An acoustic barrier installation according to claim 14, wherein there are at least two acoustic barriers and wherein a first acoustic barrier includes an output port for transmitting a sound-masking signal to a second acoustic barrier, arranged in a daisy-chain layout.

18. A kit of parts for an acoustic barrier installation in accordance with any of claim 14, the kit of parts comprising at least one acoustic barrier and a signal generator.

19. A method of mitigating noise pollution from a noise source, the method comprising:

installing an acoustic barrier installation in accordance with claim 14;

generating a sound-masking signal for the or each loudspeaker of the installation; and audibly emitting the sound-masking signal using each loudspeaker to mask noise from the noise source.

20. A flexible acoustic barrier for suspending from a support frame, comprising:

a portion of acoustic insulation material; and at least one loudspeaker configured to emit an audible sound-masking signal to mask sound from a sound source;

wherein the acoustic barrier is configured to be folded, rolled, or folded and rolled from a deployed configuration to a compact configuration; and wherein the acoustic barrier comprises a signal generator for generating a sound-masking signal for emission by the at least one loudspeaker, wherein said sound-masking signal comprises noise.

* * * * *